United States Patent [19]

Huson et al.

[11] Patent Number: 5,041,605

[45] Date of Patent: Aug. 20, 1991

[54] METHOD OF SYNTHESIZING PHENOLIC CYAN-DYE-FORMING PHOTOGRAPHIC COUPLERS

[75] Inventors: James J. Huson, Penfield; Louis F. Valente, Rochester, both of N.Y.

[73] Assignee: Eastman Kodak Company, Rochester, N.Y.

[21] Appl. No.: 439,214

[22] Filed: Nov. 20, 1989

[51] Int. Cl.$^5$ .......................................... C07C 253/30
[52] U.S. Cl. .................................. 558/417; 558/413; 558/414
[58] Field of Search ...................... 558/417, 413, 414

[56] References Cited

U.S. PATENT DOCUMENTS

| | | | |
|---|---|---|---|
| 4,333,999 | 6/1982 | Lau | 430/17 |
| 4,444,872 | 4/1984 | Kato et al. | 430/384 |
| 4,609,619 | 9/1986 | Katoh et al. | 430/553 |

OTHER PUBLICATIONS

Johnstone, et al.; Chemical Reviews, (1985), 85, pp. 129–170.

Noller, "Chemistry of Organic Compounds," 3rd ed., (1965), pp. 268 and 516, W. B. Saunders Co., Phila. & London.

*Primary Examiner*—Joseph P. Brust
*Attorney, Agent, or Firm*—Alfred P. Lorenzo

[57] ABSTRACT

Phenolic cyan-dye-forming couplers characterized by a p-cyanophenylureido group in the 2-position of the phenol are synthesized in high yield by a process comprising the steps of contacting, in a reaction solvent in the presence of a transition metal catalyst at moderate temperature and atmospheric pressure, a coupler intermediate having a nitro group in the 5-position with a hydrogen donor, such as, for example, ammonium formate, to thereby form the corresponding 2-(p-cyanophenylureido)-5-aminophenol and reacting the 2-(p-cyanophenylureido)-5-aminophenol with an acylating agent to form the phenolic cyan-dye-forming coupler.

10 Claims, No Drawings

METHOD OF SYNTHESIZING PHENOLIC CYAN-DYE-FORMING PHOTOGRAPHIC COUPLERS

FIELD OF THE INVENTION

This invention relates in general to photography and in particular to certain phenolic compounds useful as cyan-dye-forming photographic couplers. More specifically, this invention relates to an improved method for the synthesis of phenolic cyan-dye-forming couplers having a p-cyanophenylureido group in the 2-position of the phenol.

BACKGROUND OF THE INVENTION

Color images are customarily obtained in the photographic art by reaction between the oxidation product of a silver halide color developing agent (i.e., oxidized aromatic primary amino developing agent) and a dye-forming compound known as a coupler. The reaction between coupler and oxidized color developing agent results in coupling of the oxidized color developing agent at a reactive site on the coupler, known as the coupling position, and yields a dye. The dyes produced by coupling are indoaniline, azomethine, indamine, or indophenol dyes, depending upon the chemical composition of the coupler and the developing agent. The subtractive process of color image formation is ordinarily employed in multicolored photographic elements and the dyes produced by coupling are usually cyan, magenta or yellow dyes which are formed in or adjacent silver halide emulsion layers sensitive to radiation absorbed by the image dye; i.e., silver halide emulsion layers sensitive to the red, green or blue regions of the spectrum.

The couplers which typically are employed to produce cyan dyes are phenols and naphthols. They yield azomethine dyes upon coupling with oxidized aromatic primary amino color developing agents.

Phenol couplers containing a ureido group in the 2-position are described in U. K. Patent No. 1,011,940 and U.S. Pat. Nos. 3,446,622, 3,996,253, 3,758,308 and 3,880,661. These couplers generally have good light stability. However, many of them yield dyes having absorption maxima ($\lambda_{max}$) in the shorter wavelength portion of the red region of the spectrum or have relatively broad spectral absorption curves, or both. Thus, the dyes have undesirable hues for photographic purposes and frequently have significant absorption in the green region of the spectrum. In addition, a number of the dyes fade when contacted with ferrous ion and thus have poor stability in commonly employed processing compositions.

Phenolic cyan-dye-forming couplers which are characterized by a p-cyanophenylureido group in the 2-position of the phenol are highly advantageous. Such couplers are described in Lau, U.S. Pat. No. 4,333,999 issued June 8, 1982. Among the important advantages of this class of couplers are the following:

(1) They have absorption maxima ($\lambda_{max}$) in the longer wavelength portion of the red region of the visible spectrum (generally above 750 nm) and thus yield dyes of desirable hue for photographic images.

(2) They yield dyes having relatively narrow spectral absorption curves and little absorption in the green region of the spectrum and thus yield sharp cutting dyes of relatively pure hue.

(3) They yield dyes which have excellent stability toward reduction by ferrous ion and, accordingly, can be used in processes employing bleach-fix baths containing ferrous ions without a significant reduction in cyan dye density.

(4) They yield dyes which are stable to heat and light.

The phenolic cyan-dye-forming couplers of U.S. Pat. No. 4,333,999 can be prepared by a method of synthesis involving high pressure catalytic hydrogenation of a 2-(p-cyanophenylureido)-5-nitrolphenol, utilizing hydrogen gas and a transition metal catalyst in specially designed high pressure equipment, to form the corresponding 2-(p-cyanophenylureido)-5-aminophenol and reaction of the 2-(p-cyanophenylureido)-5-aminophenol with an acylating agent to form the phenolic cyan-dye-forming coupler. However, this method of synthesis requires the use of flammable hydrogen gas and specialized high pressure equipment. Moreover, impurities can be generated as a result of side reactions and thereby provide an undesirably low yield of coupler.

It is toward the objective of providing an improved method of synthesis which gives good yields and does not require the use of flammable hydrogen gas nor the use of specialized high pressure equipment that the present invention is directed.

SUMMARY OF THE INVENTION

In accordance with this invention, a phenolic cyan-dye-forming coupler characterized by a p-cyanophenylureido group in the 2-position of the phenol and having the formula:

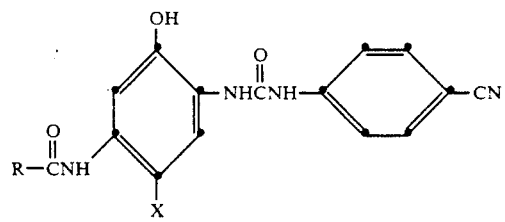

wherein:

X is hydrogen or a coupling-off group; and

R is a ballast group, is synthesized by a process comprising the steps of contacting, in a reaction solvent in the presence of a transition metal catalyst at moderate temperature and atmospheric pressure, a coupler intermediate having a nitro group in the 5-position with a hydrogen donor to thereby form the corresponding 2-(p-cyanophenylureido)-5-aminophenol and reacting the 2-(p-cyanophenylureido)-5-aminophenol with an acylating agent to form the phenolic cyan-dye-forming coupler.

Preferably, the aforesaid coupler intermediate has the formula:

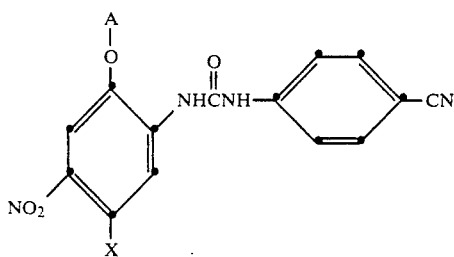

wherein A represents a hydrogen atom or a benzyl group and X is as defined above. Thus, useful coupler intermediates include 2-(p-cyanophenylureido)-5-nitrophenols which have the formula:

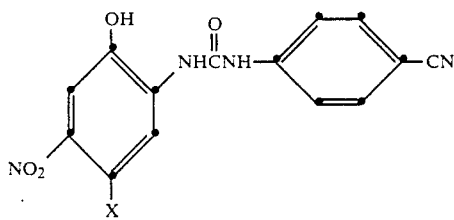

and 2-(p-cyanophenylureido)-5-nitrophenols in which the phenolic hydrogen has been replaced with a benzyl radical so that the formula becomes:

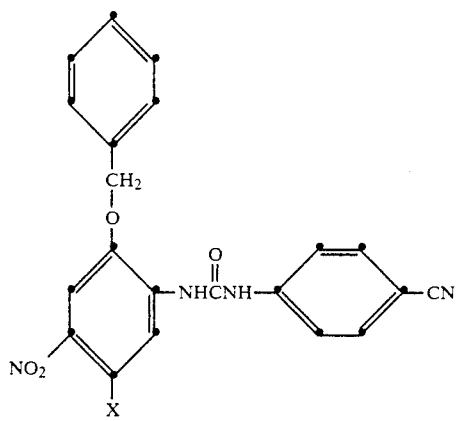

The aforesaid process provides important advntageous benefits. For example, it minimizes the formation of impurities and gives a good yield of the desired product. It also eliminates the need for the costly and hazardous use of hydrogen gas in high pressure equipment.

DESCRIPTION OF THE PREFERRED EMBODIMENTS

As indicated hereinabove, cyan-dye-forming photographic couplers prepared by the improved process of this invention are those represented by the formula:

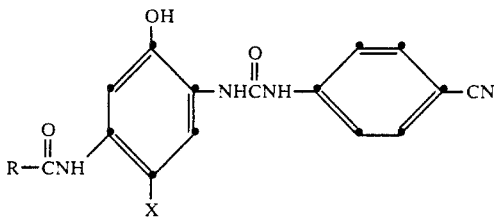

wherein:
X is hydrogen or a coupling-off group; and
R is a ballast group.

Coupling-off groups defined by X are well known to those skilled in the art. Such groups can determine the equivalency of the coupler (i.e., whether it is a two-equivalent coupler or a four-equivalent coupler), can modify the reactivity of the coupler, or can advantageously affect the layer in which the coupler is coated or other layers in the element by performing, after release from the coupler, such functions as development inhibition, bleach inhibition, bleach acceleration, color correction and the like. Representative classes of coupling-off groups include halogen, alkoxy, aryloxy, heteroyloxy, sulfonyloxy, acyloxy, acyl, heteroyl, thiocyano, alkylthio, arylthio, heteroylthio, sulfonamido, phosphonyloxy and arylazo. They are described, for example, in U.S. Pat. Nos. 2,455,169; 3,227,551; 3,432,521; 3,476,563; 3,617,291; 3,880,661; 4,052,212 and 4,134,766; and in U. K. patents and published application Nos. 1,466,728; 1,531,927; 1,533,039; 2,006,755A and 2,017,704A; the disclosures of which are incorporated herein by reference.

Examples of specific coupling-off groups are:

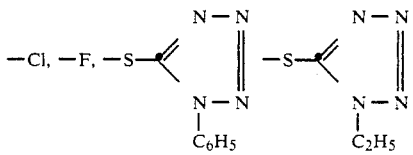

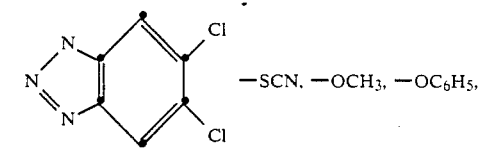

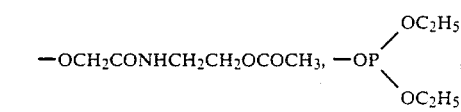

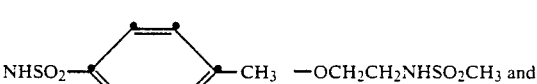

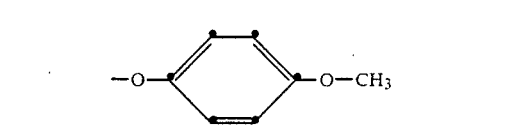

The ballast group defined by R is an organic radical of such size and configuration as to confer on the coupler molecule sufficient bulk to render the coupler substantially non-diffusible from the layer in which it is coated in a photographic element. Representative ballast groups include substituted or unsubstituted alkyl or aryl groups containing a total of 8 to 32 carbon atoms. Representative substituents include alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido, and sulfamoyl groups wherein the alkyl and aryl substituents, and the alkyl and aryl portions of the alkoxy, aryloxy, alkylthio, arylthio, alkoxycarbonyl, arylcarbonyl, acyl, acyloxy, carbonamido, carbamoyl, alkylsulfonyl, arylsulfonyl, sulfonamido and sulfamoyl substituents contain 1–30 carbon atoms and 6 to 30 carbon atoms, respectively, and can be further substituted with such substituents.

Especially advantageous couplers are those of the formula:

X is hydrogen or a coupling-off group as defined above;

Y is oxygen or sulfur;

$R^1$ is a branched alkylene group of 2 to 20 carbon atoms, i.e., a secondary or tertiary alkylene;

$R^2$ is hydroxy, carboxy, alkyl, aryl, aralkyl, alkoxyl, aryloxy, alkylsulfamoyl, arylsulfamoyl, alkylsulfonamido, arylsulfonamido, alkylsulfonyl, arylsulfonyl, alkoxycarbonyl, or acyloxy wherein the alkyl moieties of these groups contain 1 to 20 carbon atoms and the aryl moieties contain 6 to 20 carbon atoms and wherein the alkyl, aryl and aralkyl moieties can be further substituted with hydroxy, carboxy, alkoxycarbonyl or acyloxy; and n is 1 to 3.

Especially preferred are those couplers where $R^2$ is straight or branched chain alkyl of 1 to 20 carbon atoms and n is 1 to 2.

Specific couplers which can be effectively synthe-

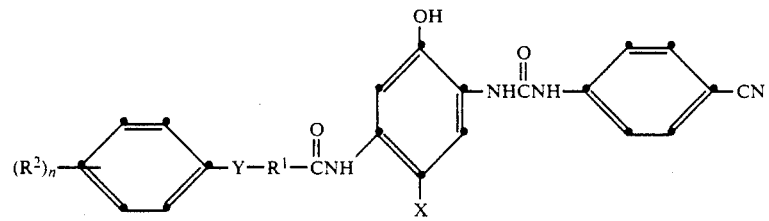

wherein:

sized by the improved method of this invention include those shown in Table I below with reference to the structural formula provided hereinabove.

TABLE I

| Coupler Number | X | R |
|---|---|---|
| 1 | —H | —CHO—⟨phenyl with $C_{15}H_{31}$-n⟩<br>$\;\;\;\;\;\;\;\;\;\;\;\;\;$|<br>$\;\;\;\;\;\;\;\;\;\;\;\;\;C_2H_5$ |
| 2 | —Cl | —CHO—⟨phenyl with $C_{15}H_{31}$-n⟩<br>$\;\;\;\;\;\;\;\;\;\;\;\;\;$|<br>$\;\;\;\;\;\;\;\;\;\;\;\;\;C_2H_5$ |
| 3 | —H | —CHO—⟨phenyl with $C_5H_{11}$-t (top), $C_5H_{11}$-t (right)⟩<br>$\;\;\;\;\;\;\;\;\;\;\;\;\;$|<br>$\;\;\;\;\;\;\;\;\;\;\;\;\;C_8H_{17}$-n |
| 4 | —H | —CHO—⟨phenyl with $C_5H_{11}$-t (top), $C_5H_{11}$-t (right)⟩<br>$\;\;\;\;\;\;\;\;\;\;\;\;\;$|<br>$\;\;\;\;\;\;\;\;\;\;\;\;\;C_{12}H_{25}$-n |
| 5 | —H | —CHO—⟨phenyl with $NHSO_2C_4H_9$-n⟩<br>$\;\;\;\;\;\;\;\;\;\;\;\;\;$|<br>$\;\;\;\;\;\;\;\;\;\;\;\;\;C_{12}H_{25}$-n |

TABLE I-continued

| Coupler Number | X | R |
|---|---|---|
| 6 | —H | —CHO—⟨C₆H₄⟩—SO₂NHC₄H₉-n<br>│<br>C₁₂H₂₅-n |
| 7 | —H | —CHO—⟨C₆H₃⟩(C₅H₁₁-t)(C₅H₁₁-t)<br>│<br>C₄H₉-n |
| 8 | —Cl | —CHO—⟨C₆H₃⟩(C₅H₁₁-t)(C₅H₁₁-t)<br>│<br>C₄H₉-n |
| 9 | —H | —CHS—⟨C₆H₄⟩—OH<br>│<br>C₁₀H₂₁-n |
| 10 | —H | —CHS—⟨C₆H₄⟩—NHCOCH₃<br>│<br>C₁₀H₂₁-n |
| 11 | —Cl | —CHO—⟨C₆H₃⟩(C₅H₁₁-t)(C₅H₁₁-t)<br>│<br>C₁₂H₂₅-n |
| 12 | —F | —CHO—⟨C₆H₃⟩(C₅H₁₁-t)(C₅H₁₁-t)<br>│<br>C₄H₉-n |
| 13 | —H | —CHO—⟨C₆H₄⟩—COCH₃<br>│<br>C₁₀H₂₁-n |
| 14 | —H | —CHO—⟨C₆H₄⟩—C(CH₃)₂—⟨C₆H₄⟩—OCOCH₃<br>│<br>C₁₀H₂₁-n |
| 15 | —H | —CHO—⟨C₆H₄⟩—C(CH₃)₂—⟨C₆H₄⟩—OH<br>│<br>C₁₀H₁₁-n |
| 16 | —H | —CHO—⟨C₆H₄⟩—COOH<br>│<br>C₁₀H₂₁-n |
| 17 | —NHSO₂—⟨C₆H₄⟩—CH₃ | —CHO—⟨C₆H₃⟩(C₅H₁₁-t)(C₅H₁₁-t)<br>│<br>C₄H₉-n |

TABLE I-continued

| Coupler Number | X | R |
|---|---|---|
| 18 | 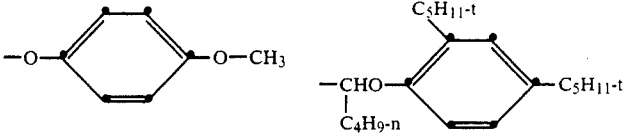 —O—⟨benzene⟩—O—CH₃ | 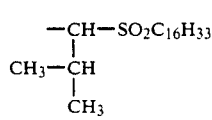 —CHO—⟨benzene with $C_5H_{11}$-t and $C_5H_{11}$-t⟩<br>    $\mid$<br>    $C_4H_9$-n |
| 19 | —H | —CH—SO$_2$C$_{16}$H$_{33}$<br>    $\mid$<br>CH$_3$—CH<br>          $\mid$<br>          CH$_3$ |
| 20 | —O—⟨benzene⟩—O—CH₃ | —CH—SO$_2$C$_{16}$H$_{33}$<br>    $\mid$<br>CH$_3$—CH<br>          $\mid$<br>          CH$_3$ |

The improved process of this invention is carried out with the use of moderate temperatures, for example, a temperature in the range of about 20° C. to about 60° C., and atmospheric pressure. Useful transition metal catalysts include palladium on carbon, palladium on alumina, palladium on sulfided carbon and Raney nickel. The catalyst can be employed in any catalytically effective amount.

Useful hydrogen donors include formic acid, sodium formate, ammonium formate, triethylammonium formate, hypophosphorus acid, sodium hypophosphinate, triethylammonium hypophosphinate and hydrazine.

Useful reaction solvents include ethyl acetate, acetonitrile, methanol, isopropanol, tetrahydrofuran, formic acid, and N,N-dimethylformamide. The same compound, for example, formic acid, can be used as both the reaction solvent and the hydrogen donor. Reaction solvents consisting of a mixture of two or more compounds can be advantageously employed.

In the process of this invention, the 2-(p-cyanophenylureido)-5-aminophenol is typically reacted in situ, that is without isolation, with an acylating agent to form the phenolic cyan-dye-forming coupler. Suitable acylating agents include acid halides and anhydrides derived from aliphatic or aromatic carboxylic acids. The preferred acylating agents for the purpose of this invention are acyl chlorides of the formula

where R is as defined hereinabove.

The invention is further illustrated by the following examples of its practice.

EXAMPLE 1

In this example, coupler No. 7 was synthesized by a reaction sequence involving hydrogenation of an intermediate having the formula:

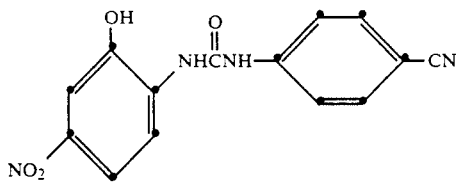

to thereby form the corresponding aminophenol having the formula:

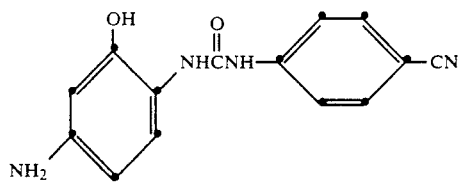

followed by reaction in situ with an acyl chloride of the formula:

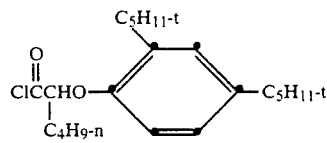

to thereby form coupler No. 7.

In carrying out this reaction sequence, 15.0 grams (0.05 moles) of compound I, 15.0 grams (0.24 moles) of ammonium formate and 1.5 grams of a palladium on carbon catalyst composed of carbon loaded with 5% by weight of palladium were added to a reaction solvent consisting of 75 milliliters of tetrahydrofuran and 5 milliliters of water. The reaction mixture was stirred for four hours at room temperature and atmospheric pressure with the exothermic heat of reaction increasing the temperature to 30° C. At the end of this period, 24.8 grams (0.068 moles) of compound III in 75 milliliters of ethyl acetate was added over a period of 10 minutes. The reaction mixture was filtered, rinsed with 50 milliliters of ethyl acetate, washed with 50 milliliters of hydrochloric acid, washed with 50 milliliters of a sodium chloride solution, dried, filtered and combined with 180 milliliters of toluene. After standing overnight, the temperature was reduced to 10° C. to effect crystallization and the crystals were collected, rinsed with 50 milliliters of cold toluene, washed with 50 milliliters of heptane, and dried in a vacuum oven at 40° C. The yield of coupler was 23.5 grams, which is equal to 78% of the theoretical yield.

EXAMPLE 2

In this example, coupler No. 19 was synthesized by a reaction sequence involving hydrogenation of an intermediate having the formula:

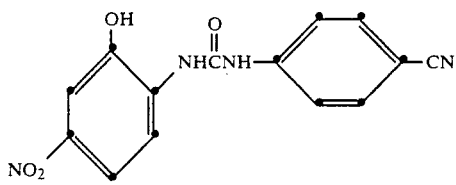
I.

to thereby form the corresponding aminophenol having the formula:

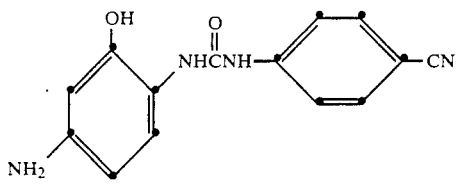
II.

followed by reaction in situ with an acyl chloride of the formula:

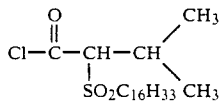
III.

to thereby form coupler No. 19.

In carrying out this reaction sequence, 15.0 grams (0.05 moles) of compound I was added to a 250-milliliter round bottom 4-necked flask containing 70 milliliters of tetrahydrofuran and 10 milliliters of isopropyl alcohol. To the yellow reaction slurry there was added 11 grams (0.175 moles) of ammonium formate followed by 1.5 grams of a palladium on sulfided-carbon catalyst. The flask was connected to a condenser and the reaction slurry was heated to 50° C. with stirring for 4 hours. After the reduction was complete, the reaction mixture was cooled to 25° C. whereupon 3.2 grams of ammonium formate was added, followed by dropwise addition of 55.2 grams of a 44.5 weight % solution of compound III in ethyl acetate over a period of 10 minutes. As a result of the exothermic heat of reaction, the temperature of the reaction mixture increased from 25° C. to 40° C. Stirring was continued for 30 minutes.

Fifty milliliters of water was added to the reaction mixture to solubilize the salts generated and 10 milliliters of concentrated HCl was added dropwise over 15 minutes. The resulting two-phase system was stirred for 15 minutes, filtered and then washed with 50 milliliters of ethyl acetate followed by 10 milliliters of water. The layers were allowed to separate in a separatory funnel for 15 minutes and the bottom aqueous layer was removed and discarded. The organic layer was then washed with 50 milliliters of brine and the layers were allowed to separate for 15 minutes. The lower aqueous layer was discarded and the organic layer was dried over anhydrous magnesium sulfate. After filtering and drying, the organic layer was concentrated under reduced pressure with 50° C. heat, followed by a 25 milliliter flash with acetic acid. The product was added to a mixture of 80 milliliters of acetic acid and 40 milliliters of heptane, heated to 40° C., held one hour, cooled to 30° C., held one hour, cooled to 20° C., held one hour, cooled to 10° C., collected, washed with 25 milliliters of acetic acid, and dried overnight in a vacuum oven at 45° C. The dried product was added to 100 milliliters of methanol, warmed to 40° C., held 15 minutes, cooled to 5° C., stirred for 2 hours, collected, washed with 50 milliliters of cold methanol and dried overnight in a vacuum oven at 45° C. The yield of coupler was 24.75 grams, which is equal to 74% of the theoretical yield.

EXAMPLE 3

In this example, coupler No. 20 was synthesized by a reaction sequence involving hydrogenation of an intermediate having the formula:

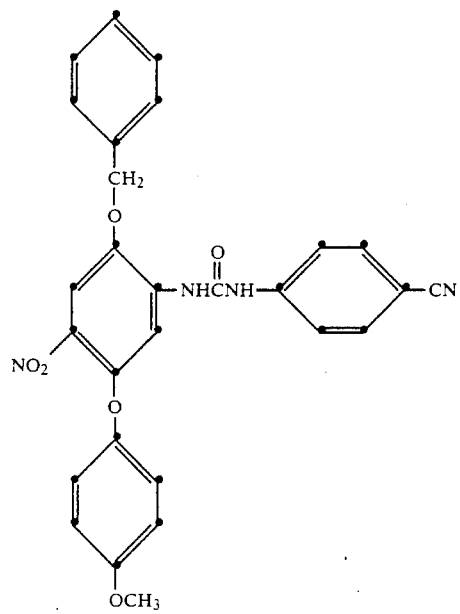
I.

to thereby form the corresponding aminophenol having the formula:

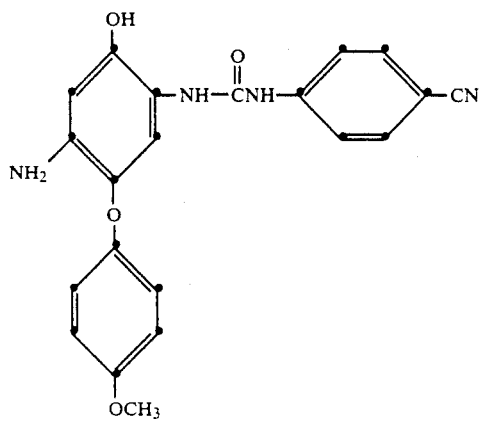

followed by reaction in situ with an acyl chloride of the formula:

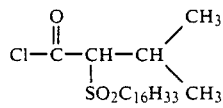

to thereby form coupler No. 20.

In carrying out this reaction sequence, 5.1 grams of compound I, 2.9 grams of ammonium formate, 20 milliliters of tetrahydrofuran, 20 milliliters of isopropyl alcohol and 0.33 grams of a palladium on alumina catalyst were added to a 100-milliliter round bottom flask. The reaction mixture was stirred for 18 hours and then 10.6 grams of compound III was added and stirring was continued for one-half hour. Fifteen milliliters of hydrochloric acid was added dropwise, and the two-phase mixture was filtered to remove the catalyst. The layers were allowed to separate, and the organic layer was washed, filtered and dried under vacuum. The yield of coupler was 5.3 grams, which is equal to 70% of the theoretical yield.

EXAMPLE 4

In this example, coupler No. 18 was synthesized by a reaction sequence involving hydrogenation of an intermediate having the formula:

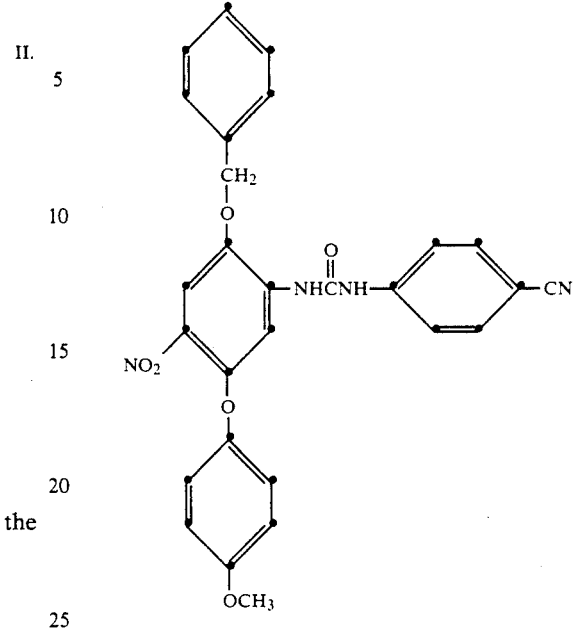

to thereby form the corresponding aminophenol having the formula:

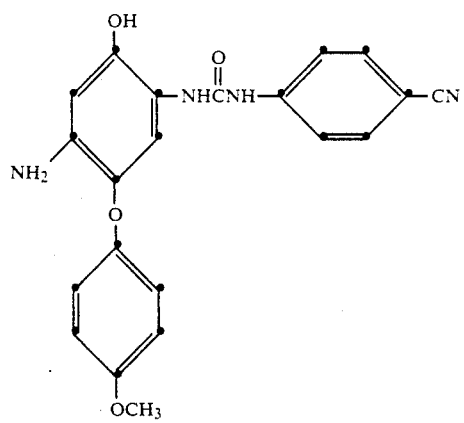

followed by reaction in situ with an acyl chloride of the formula:

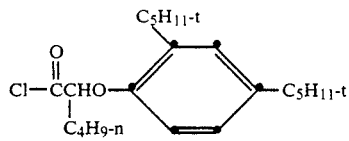

to thereby form coupler No. 18.

In carrying out this reaction sequence, 20.4 grams (0.04 moles) of compound I, 100 milliliters of tetrahydrofuran, 60 milliliters of isopropyl alcohol, 11 grams of ammonium formate, and 1 gram of a palladium on sulfided-carbon catalyst were added to a 250-milliliter round bottom flask. The reaction mixture was heated to 50° C. and held for three hours. Forty milliliters of hydrochloric acid and 15 milliliters of sodium chloride solution were added and the mixture was stirred for 15 minutes, filtered and washed with ethyl acetate. The layers were allowed to separate and the aqueous layer was discarded. The organic layer was washed with sodium chloride solution, and the aqueous layer was discarded. To the organic layer, there was added 17.6 grams (0.048 moles) of compound III dissolved in 15 milliliters of ethyl acetate. The reaction mixture was stirred for 15 minutes, 12 grams of ammonium acetate dissolved in 20 milliliters of water was added, stirring was continued for 30 minutes and the layers were allowed to separate. The aqueous layer was discarded, and the organic layer was washed with 25 milliliters of 20% NaCl, dried with 10 grams of anhydrous MgSO₄, filtered and placed under vacuum to remove the solvents. The solvents were removed to an oil at 40 to 45° C., 40 milliliters of acetonitrile was added and removed to an oil. To this oil was added 140 milliliters of acetonitrile and 20 milliliters of methanol. The mixture was heated to 60° C. to dissolve the oil and the solution was seeded. The mixture was stirred overnight at room temperature then cooled to 5° C. and the solid was collected on a funnel and washed. The yield of coupler was 20.2 grams, which is equal to 70% of the theoretical yield.

As the above examples demonstrate, the method of this invention does not require the use of flammable hydrogen gas nor the use of specialized high pressure equipment as has been employed in the prior art. Moreover, good yields in the range of 70 to 78 percent of theoretical were obtained by the catalytic transfer hydrogenation process of this invention.

The invention has been described in detail with particular reference to preferred embodiments thereof, but it will be understood that variations and modifications can be effected within the spirit and scope of the invention.

What is claimed is:

1. A process for the synthesis of a phenolic cyan-dye-forming photographic coupler characterized by a p-cyanophenylureido group in the 2-position of the phenol and having the formula:

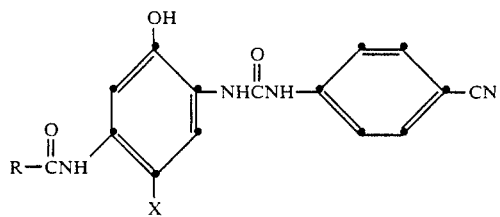

wherein:

X is hydrogen or a coupling-off group; and

R is a ballast group, comprising the steps of contacting, in a reaction solvent in the presence of a transition metal catalyst at moderate temperature and atmospheric pressure, a coupler intermediate having a nitro group in the 5-position with a hydrogen donor to thereby form the corresponding 2-(p-cyanophenylureido)-5-aminophenol and reacting said 2-(p-cyanophenylureido)-5-aminophenol with an acylating agent to form said phenolic cyan-dye-forming photographic coupler.

2. A process for the synthesis of a phenolic cyan-dye-forming photographic coupler characterized by a p-cyanophenylureido group in the 2-position of the phenol and having the formula:

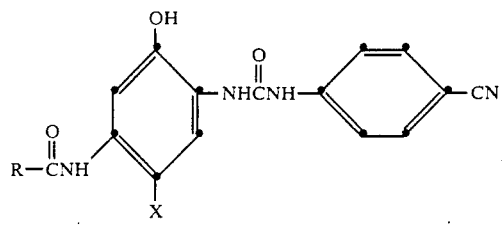

wherein X is hydrogen or a coupling-off group and R is a ballast group; comprising the steps of contacting, in a reaction solvent in the presence of a transition metal catalyst at moderate temperature and atmospheric pressure, a coupler intermediate of the formula:

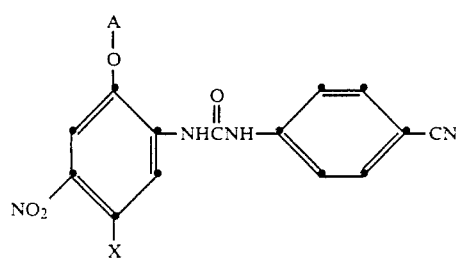

where A is a hydrogen atom or a benzyl group and X is as defined above, with a hydrogen donor to thereby form the corresponding 2-(p-cyanophenylureido)-5-aminophenol and reacting said 2-(p-cyanophenylureido)-5-aminophenol with an acyl chloride of the formula:

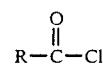

where R is as defined above, to thereby form said phenolic cyan-dye-forming photographic coupler.

3. The process as claimed in claim 2 wherein the reaction temperature is in the range of from about 20° C. to about 60° C.

4. The process as claimed in claim 2 wherein said transition metal catalyst comprises palladium.

5. The process as claimed in claim 2 wherein said reaction solvent comprises tetrahydrofuran.

6. The process as claimed in claim 2 wherein said hydrogen donor is ammonium formate.

7. A process as claimed in claim 2 wherein said coupler intermediate has the formula:

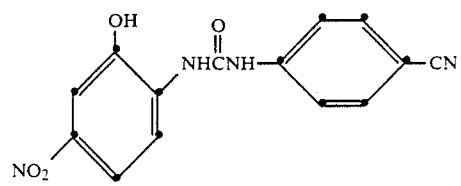

and said acyl chloride has the formula:

8. A process as claimed in claim 2 wherein said coupler intermediate has the formula:
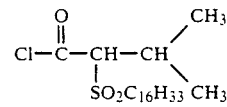
and said aryl chloride has the formula:
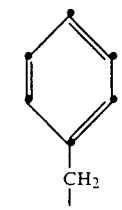
9. A process as claimed in claim 2 wherein said coupler intermediate has the formula:
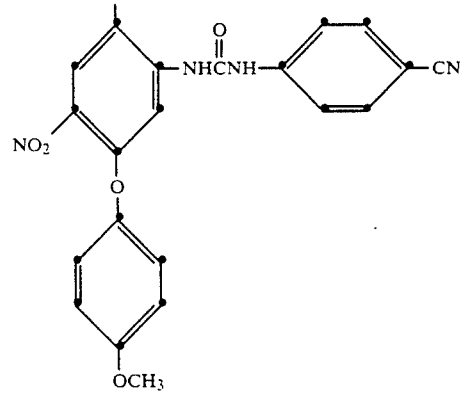
and said acyl chloride has the formula:
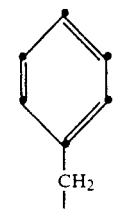
10. A process as claimed in claim 2 wherein said coupler intermediate has the formula:
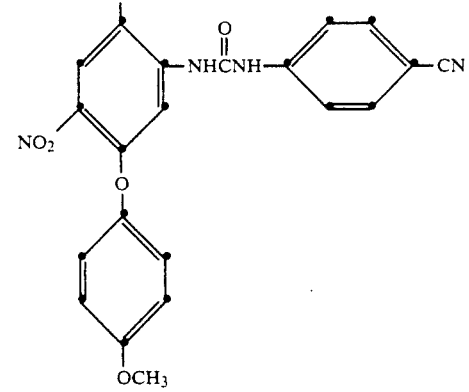
and said acyl chloride has the formula:
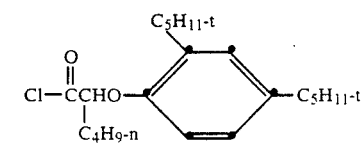
* * * * *